United States Patent [19]
Leever

[11] Patent Number: 5,738,515
[45] Date of Patent: Apr. 14, 1998

[54] APPARATUS AND METHOD FOR POSITIONING A MIXILLARY DENTAL ARCH MODEL IN AN ARTICULATOR

[76] Inventor: David L. Leever, 9806 N. 56th St., Temple Terrace, Fla. 33617

[21] Appl. No.: 798,220

[22] Filed: Feb. 10, 1997

Related U.S. Application Data

[63] Continuation-in-part of Ser. No. 594,047, Jan. 30, 1996, abandoned.

[51] Int. Cl.$^6$ ................................................. A61C 11/00
[52] U.S. Cl. ............................. 433/55; 433/56; 433/63
[58] Field of Search ................................. 433/55, 56, 62, 433/63

[56] References Cited

U.S. PATENT DOCUMENTS

| | | | |
|---|---|---|---|
| 1,052,806 | 2/1913 | Evans | 433/73 |
| 2,225,274 | 12/1940 | MacGoun | 433/73 |
| 2,334,643 | 11/1943 | Moore | 433/56 |
| 2,613,440 | 10/1952 | Murray et al. | 433/55 |
| 2,621,406 | 12/1952 | McPhee | 433/55 |
| 2,748,481 | 6/1956 | Glueck | 433/55 |
| 2,772,477 | 12/1956 | Miller | 433/55 |
| 2,959,857 | 11/1960 | Stoll | 433/55 |
| 3,200,497 | 8/1965 | Goodfriend | 433/44 |
| 3,218,716 | 11/1965 | Stuart | 433/73 |
| 3,336,670 | 8/1967 | Heydenreich | 433/56 |
| 3,854,208 | 12/1974 | Arant | 433/73 |
| 4,391,589 | 7/1983 | Monfredo et al. | 433/63 |
| 4,501,556 | 2/1985 | Zelnigher | 433/56 |
| 4,609,351 | 9/1986 | Blair | 433/55 |
| 4,624,639 | 11/1986 | Wong | 433/56 |
| 5,160,262 | 11/1992 | Alpern et al. | 433/59 |

OTHER PUBLICATIONS

Dawson, Peter E., "Evaluation, Diagnosis and Treatment of Occlusal Problems", second edition, St. Lois, MO, The C.V. Mosby Co., 1989, p. 29.

McMinn, R.M.H., "Color Atlas of Head and Neck Anatomy", Chicago, IL, Year Book Medical Publishers, Inc., 1981, pp. 10–23.

Jacobson, Alexander, "Radiographic Cephalometry: From Basics Videoimaging", Carol Stream, IL, Quintessence Publishing Co., Inc., 1995, pp. 276–303.

Thurow, Raymond C., "Edgewise Orthodontics", St. Lois, MO, The C.V. Mosby Co., 1966, pp. 261–262.

Primary Examiner—John J. Wilson
Attorney, Agent, or Firm—C. Douglas McDonald, Jr. & Associates, P.A.

[57] ABSTRACT

The present invention generally relates to an apparatus and method for positioning a maxillary dental arch model in a dental articulator to simulate the positioning of a maxillary dental arch represented by the arch model. The arch model may be positioned on a plate having a substantially planar surface with a fulcrum point through which three generally mutually perpendicular axes are aligned. In addition, the plate may be movably mounted to an articulator and adjusted with respect to these axes based upon three linear and three angular measurements related to the positioning of a patient's maxillary dental arch in the patient's skull.

20 Claims, 14 Drawing Sheets

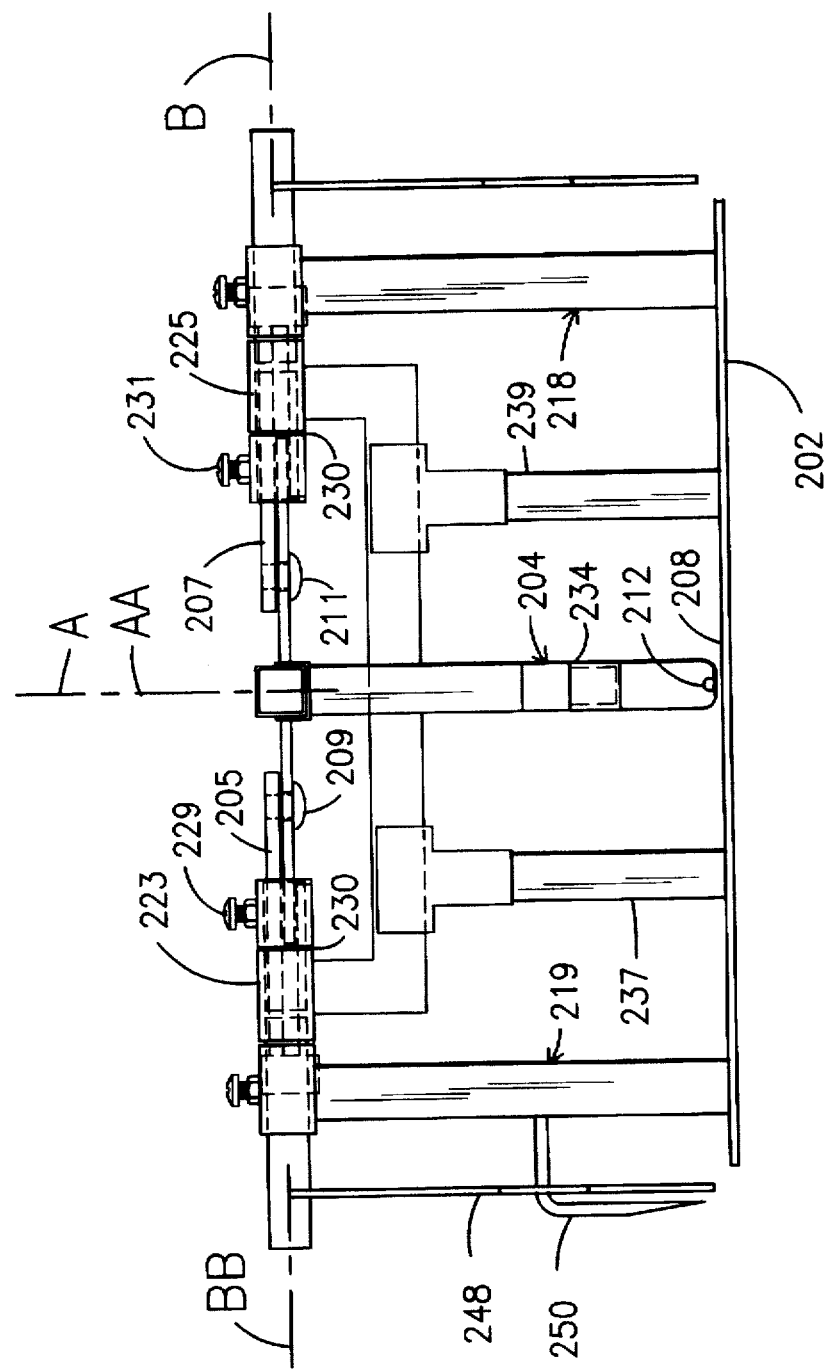

APPARATUS AND METHOD FOR POSITIONING A MIXILLARY DENTAL ARCH MODEL IN AN ARTICULATOR

RELATED APPLICATION

This application is a continuation-in-part of application Ser. No. 08/594,047, entitled Apparatus and Method for Positioning a Maxillary Dental Arch Model in an Articulator, filed Jan. 30, 1996 and now abandoned.

BACKGROUND OF THE INVENTION

This invention relates generally to an apparatus and method for positioning a maxillary dental arch model in a dental articulator. More particularly, it relates to an apparatus and a method for quantifying the position of a maxillary dental arch in an individual's skull and transferring a dental arch model to a dental articulator based upon these quantified measurements.

Facebow recording has classically been the preferred method for transferring the location of the so-called condylar hinge axis in the patient's skull to a dental articulator and positioning a dental arch model with respect to this location. Typically, the mandibular dental arch model is positioned with respect to this transferred axis by use of a centric bite record for positioning the lower dental arch model against the upper arch model. The closure of the vertical opening between the upper and lower dental arch models created by the bite record will maintain the accuracy of the bite record only if the path of closure on the articulator is the same as the path of closure on the patient. This accuracy is directly related to the maxillary cast transfer procedure.

In general, the amount of accuracy involved in transferring procedures is related to the proficiency of the technician performing such procedures. Invariably, some amount of human error is introduced into the transferring procedure, such as, during the initial placement of the facebow on the patient, recording the measurements from the facebow or when transferring these measurements to the articulator. In addition, the amount of accuracy in positioning the models also depends largely in part upon the particular geometry of the facebow and the extent to which the articulator accurately simulates a patient's mandibular path of closure.

Another possible inadequacy with conventional facebow recording is that each time a technician desires to transfer a dental arch model to an articulator, a facebow corresponding to the particular patient is required. This approach generally necessitates either the laborious process of refitting a patient with a facebow or retaining a voluminous stock of facebows. It is reemphasized that the success in evaluation, diagnosis and treatment of occlusal problems utilizing a conventional facebow transfer depends to a large extent on the accuracy in mounting the facebow on the patient, transferring it to the articulator and positioning the arch models as well as the particular design of the facebow apparatus.

The transferring of a maxillary dental arch model to the articulator becomes increasingly important when employing the generally more precise dental articulators, such as the polycentric hinge joint articulators. As dental articulators more accurately reproduce mandibular movement, an accurate recording of the maxillary cast orientation relative to the condyle/fossa centric relation position becomes essential.

SUMMARY OF THE INVENTION

In view of the foregoing, it is desired to provide an apparatus and method to position a maxillary dental arch model accurately in an articulator that may be adapted for use with all types of dental articulators. Such an apparatus and method should also take advantage of anatomical features and the relationships of such features as to provide reproducible measurements for positioning arch models, obviating the need for maintaining a bulky supply of facebows. It is also desired that an apparatus and method provide a simplified approach to transfer a maxillary dental arch model to an articulator that requires less subjective skill than the conventional, often cumbersome facebow approach for achieving accurate positioning of the upper arch model.

In view of the foregoing the present invention provides an apparatus and method for positioning a maxillary dental arch model in a dental articulator to simulate the occlusal contact plane of a maxillary dental arch in a skull. The apparatus of the present invention includes a platform for receiving the maxillary dental arch model, with the platform having a generally planar top surface and a front edge, with a fulcrum positioned proximal to the front edge of the platform. An arm is attached to the platform to position the fulcrum at a predetermined position, with the arm being dimensioned and configured for removable attachment to the articulator. The apparatus also includes means for adjustably rotating the top surface of the platform about three generally mutually perpendicular axes that intersect at the fulcrum, with the arm including means to linearly adjust the fulcrum along at least one of the axes, whereby the orientation of the platform may be adjusted to stimulate the positioning of the occlusal contact plane of a maxillary dental arch.

The method of the present invention is directed to the same purpose as the apparatus and includes positioning the occlusal contact plane of a maxillary dental arch model on the substantially planar surface such that the midpoint between the front incisors of the dental arch model is substantially aligned with the fulcrum point. The method also includes rotating the substantially planar surface of the plate about a substantially horizontal first axis, rotating the substantially planar surface about another substantially horizontal axis that is substantially normal to the first axis and rotating the substantially planar surface about a substantially vertical third axis that is substantially normal to the first axis and the second axis in order to simulate the positioning of the occlusal contact plane of the dental arch. The method of the present invention further includes adjusting the fulcrum along the second axis and adjusting the fulcrum along the first axis to simulate the positioning of the dental arch in the skull. A preferred embodiment of the present invention also includes positioning the fulcrum point along the third axis to further simulate the positioning of the midpoint between the front incisors in the skull.

BRIEF DESCRIPTION OF THE DRAWINGS

For a fuller understanding of a preferred embodiment of the nature and objects of the present invention, reference should be had to the following detailed description taken in connection with the accompanying drawings, in which:

FIG. 14 is a front view of the apparatus and calibration stand of FIG. 12;

DETAILED DESCRIPTION

Figure 1:
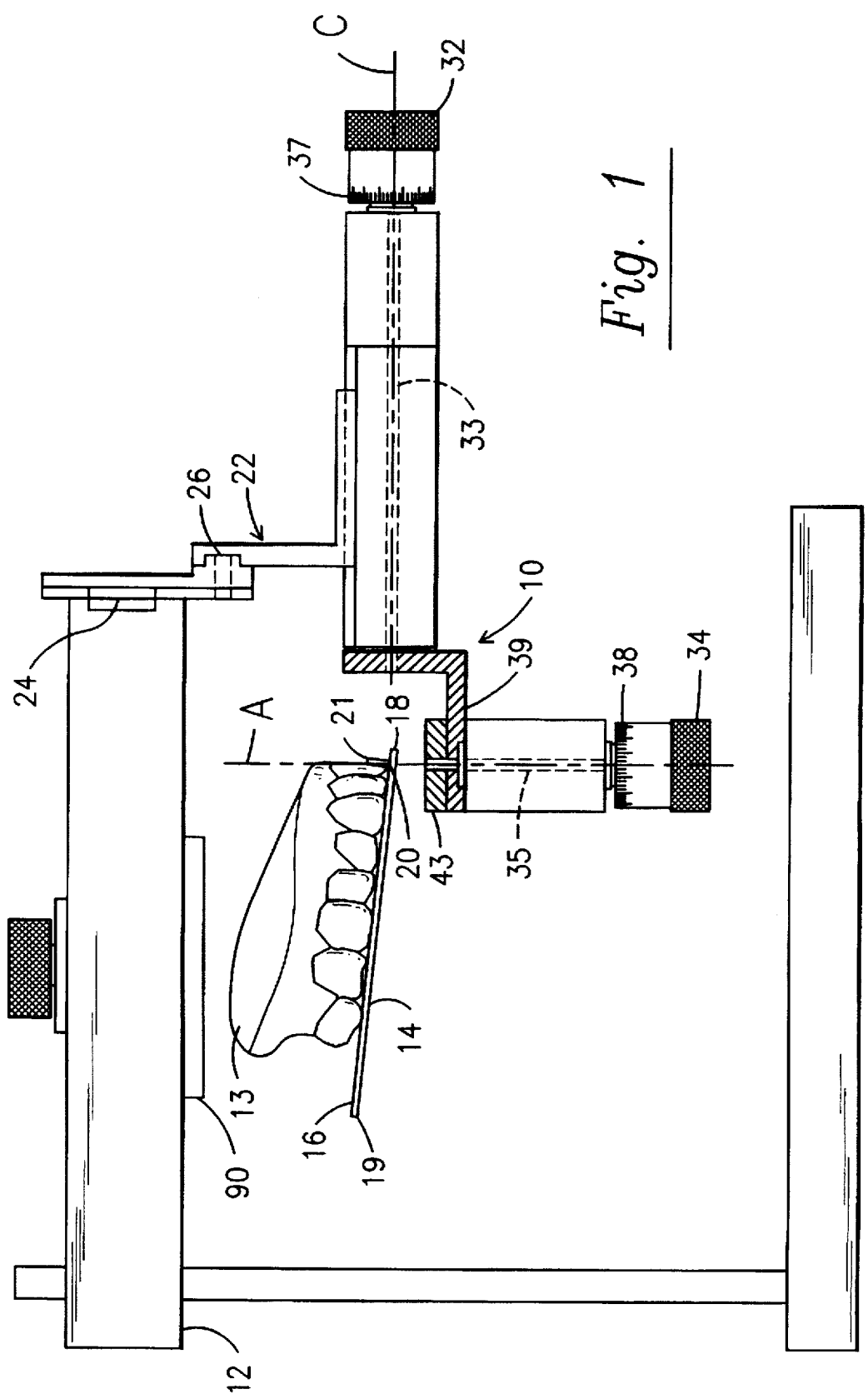
FIG. 1 is a side elevation of a preferred embodiment of the apparatus of the present invention attached to a dental articulator and supporting a maxillary dental arch model with a portion of the plate housing and the first rotating means removed.

Preferred embodiments of the apparatus of the present invention is illustrated in FIGS. 1–5 and 9–16, in which similar reference characters refer to similar parts throughout the several views of the drawings. As shown in FIG. 1, a preferred embodiment of the apparatus of the present invention is illustrated as attached to a dental articulator 12 and supporting a maxillary dental arch model 13. It will be appreciated by those skilled in the art that the apparatus 10 of the present invention may be used with substantially any dental articulator, including the conventional as well as the modern polycentric hinge joint articulators. The physical attachment of the apparatus 10 to each articulator 12 will generally require minor modifications according to the design of the particular articulator 12.

The present invention generally provides an apparatus and a method primarily intended for positioning a maxillary dental arch model in a dental articulator to simulate the positioning of the occlusal contact plane of a dental arch in a patient's skull. The measurements employed to position the dental arch model in the articulator are based, in some part, upon a predetermined point in the maxillary occlusal contact plane, which is preferably the front incisal edge of the midpoint between the front incisors. In addition, rather than relying upon the geometry of the particular measuring apparatus, such as with conventional facebow recording and transferring approaches, the present invention relies substantially upon relationships between predetermined anatomical reference points from which a technician may simulate the positioning of a patient's maxillary arch in a dental articulator of choice.

In essence, the present invention provides a convenient approach to obtaining reproducible measurements for positioning a patient's maxillary dental arch model in a dental articulator. Three linear measurements identify a point in space that preferably corresponds to the midpoint between the front incisors of the patient's dental arch and additional measurements, angular, linear or a combination thereof, define how the patient's occlusal contact plane lies in that space. These measurements are then preferably transferred to the apparatus 10 of the present invention in order to simulate the positioning of the patient's dental arch in his or her skull. A primary factor in obtaining an accurate translation to the dental articulator is an identifiable and reproducible point common to all measurements, which conveniently may be the midpoint between the front incisors.

Figure 2:
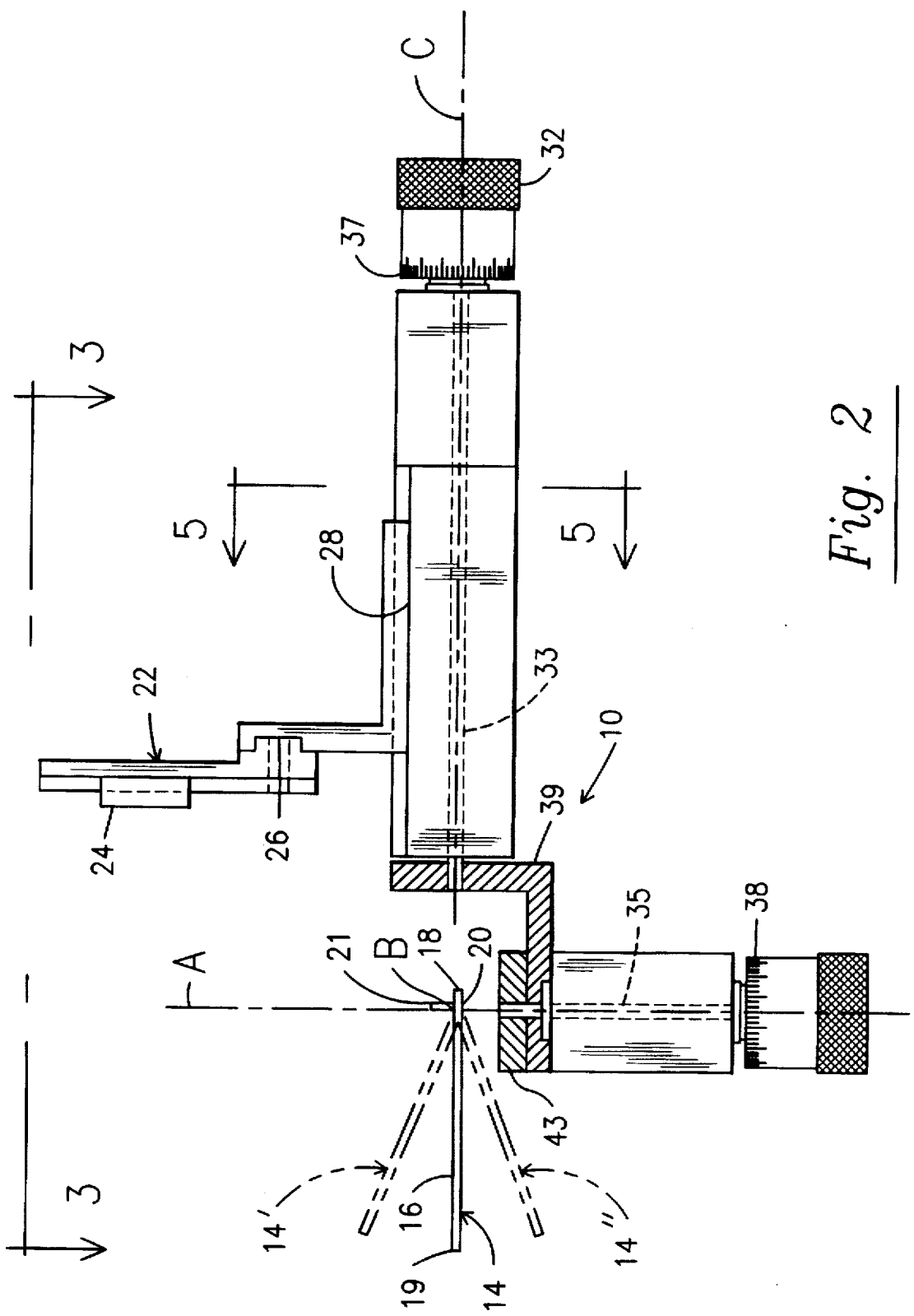
FIG. 2 is the apparatus of FIG. 1 removed from the dental articulator and without the arch model.
Figure 3:
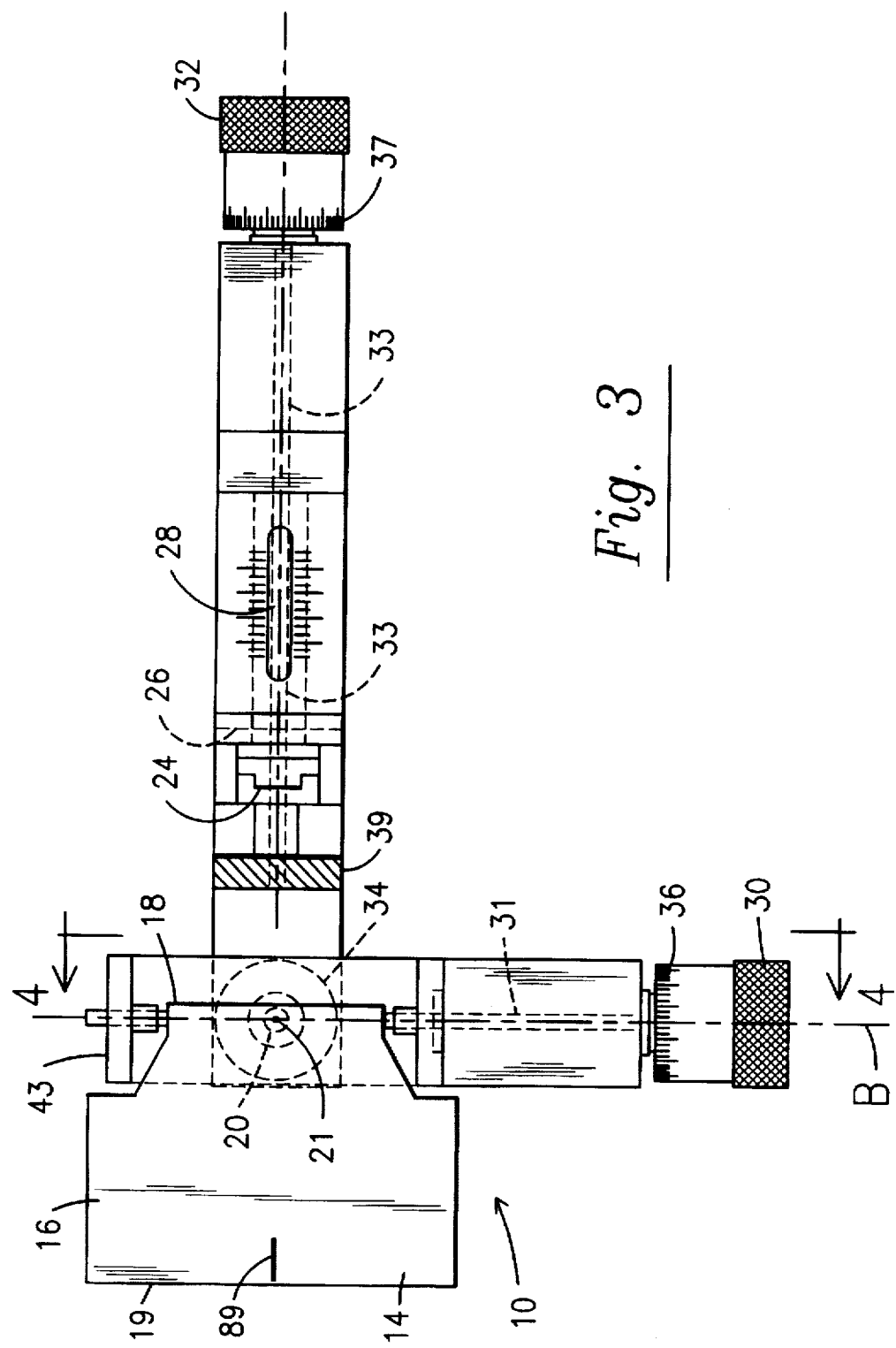
FIG. 3 is a top view of the apparatus of FIG. 2 taken along line 3—3.
Figure 5:
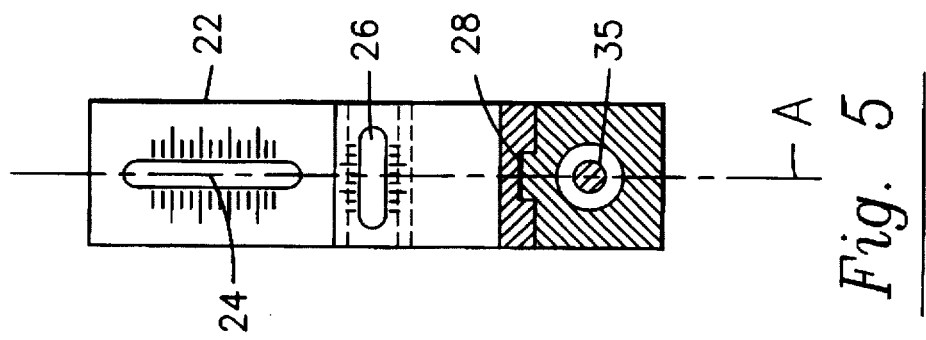
FIG. 5 is a front view of the arm and second rotating means taken along lines 5—5 of the apparatus in FIG. 2.
Figure 4:
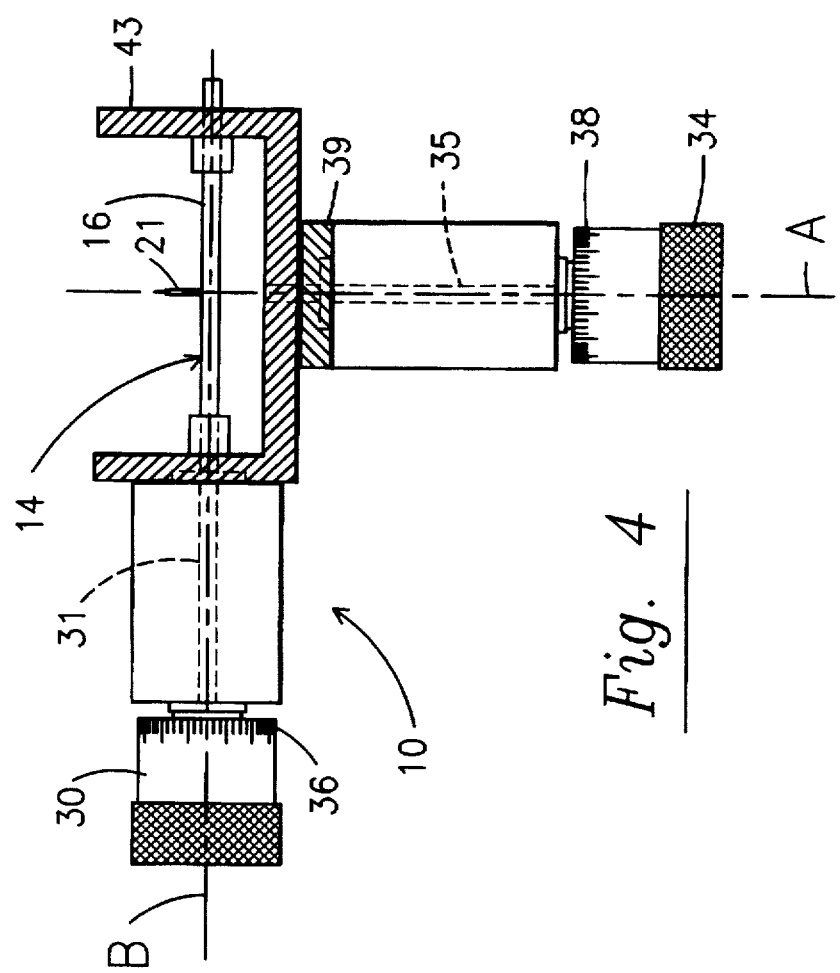
FIG. 4 is a front view of the apparatus of FIG. 3 taken along line 4—4.
Figure 9:
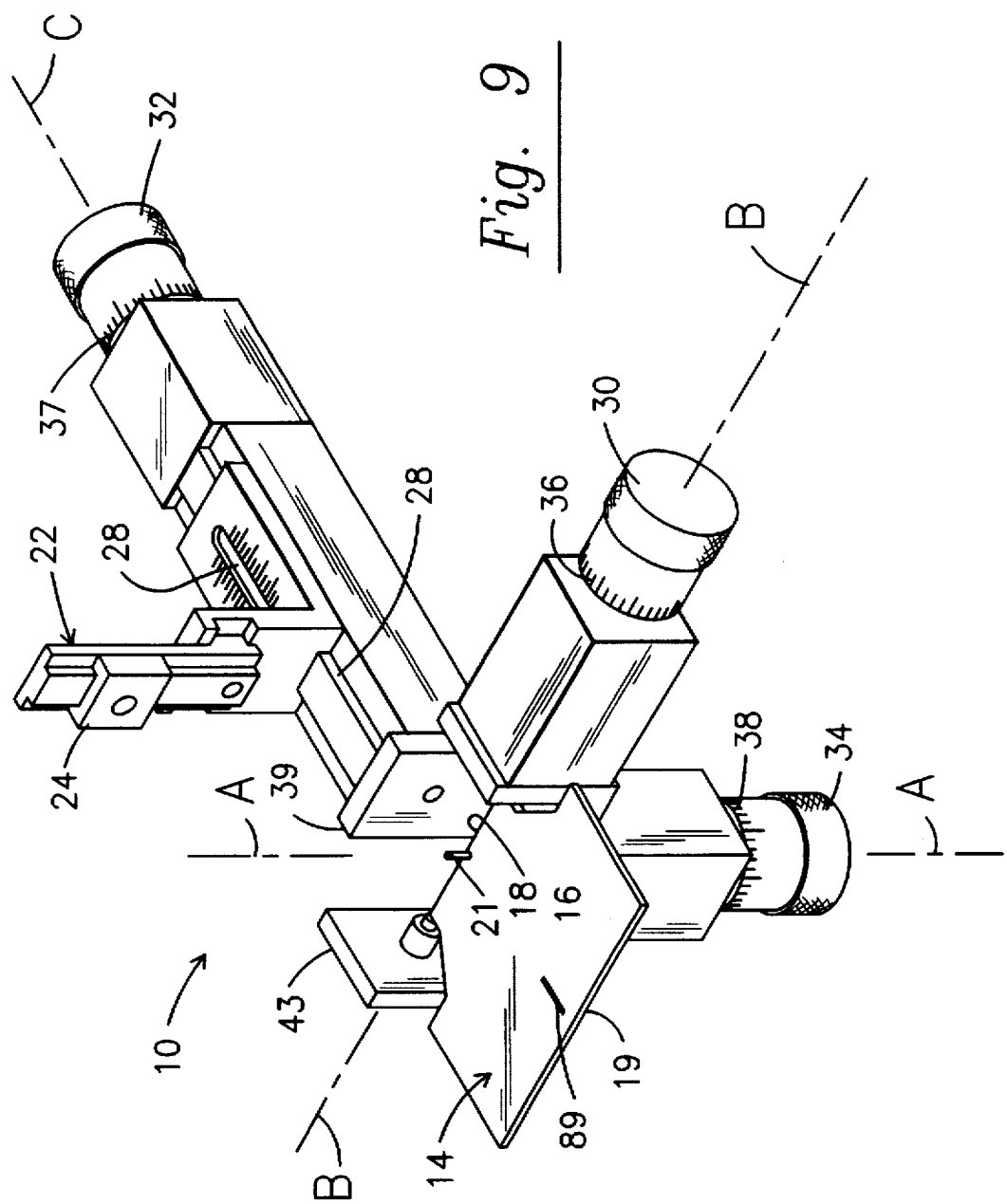
FIG. 9 is a perspective view of a preferred embodiment of the apparatus of the present invention.

As shown in FIGS. 1, 2, and 9, the apparatus of the present invention includes an adjustable plate 14 for receiving the maxillary dental arch model 13. The plate 14 further includes a generally planar top surface 16 and a front edge 18. A fulcrum 20 is positioned on the top surface 16 of the plate 14 proximal the front edge 18 for aligning the midpoint 42 between the front incisors of the dental arch model 13 that is to be positioned upon the plate 14. Preferably, an alignment pin 21 is attached to the plate 14 aligned with the fulcrum point 20 and extending substantially normal from the top surface 16. This generally facilitates the initial positioning and alignment of a dental arch model 13 upon the plate 14.

Figure 10:
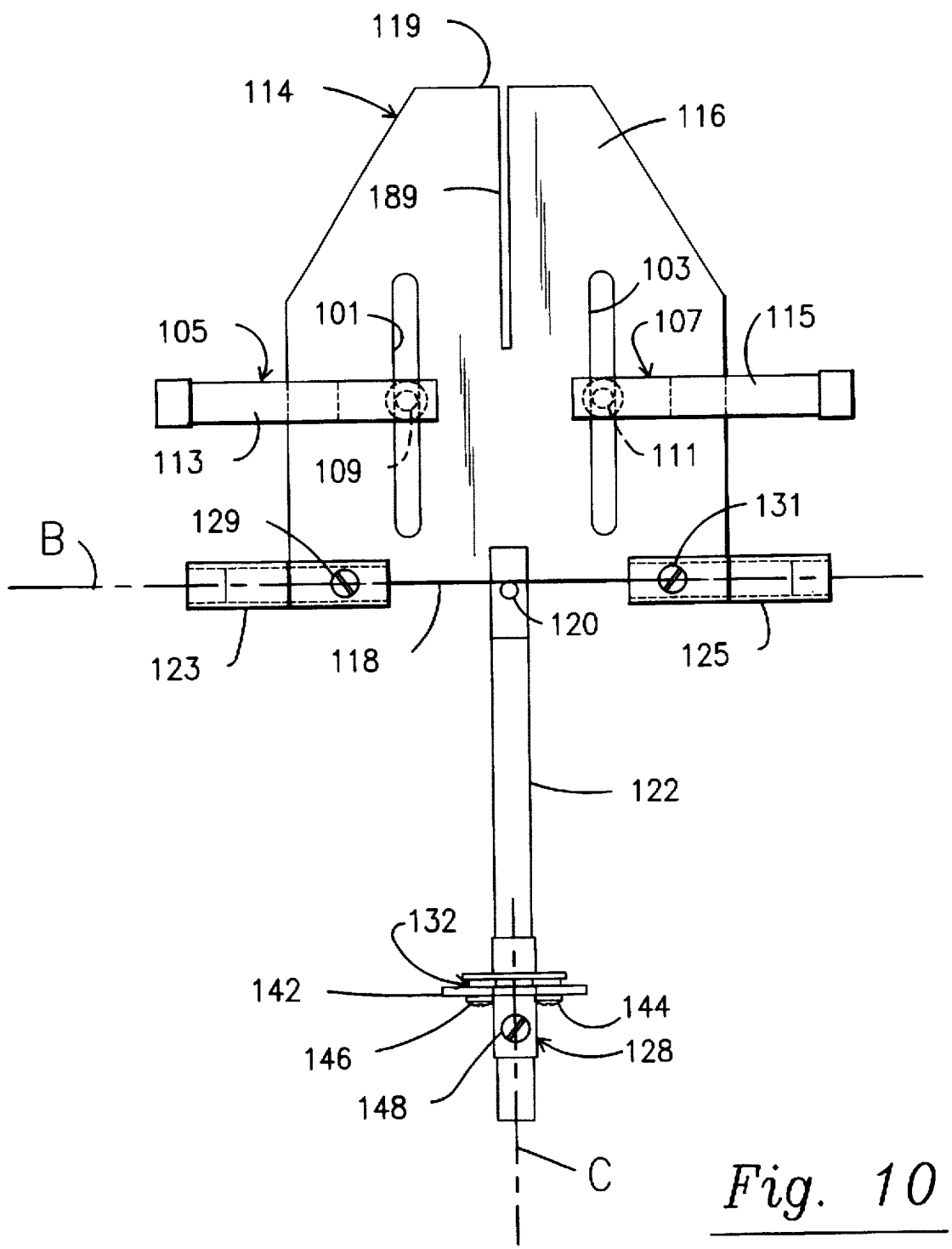
FIG. 10 is a top view of an alternative preferred embodiment of the apparatus of FIG. 2.
Figure 11:
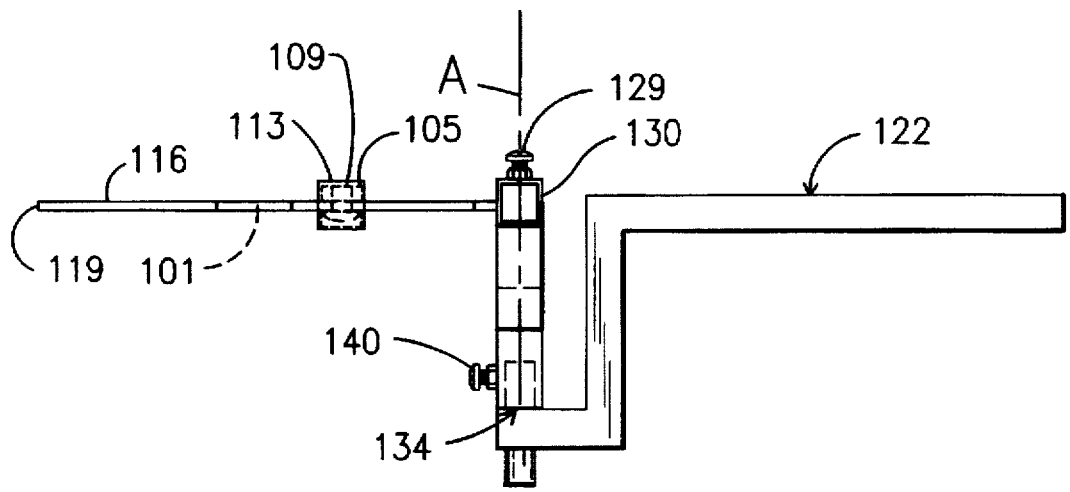
FIG. 11 is a side elevation of the apparatus of FIG. 10 with the positioning element removed.

An alternative preferred embodiment of plate 14 is shown in FIG. 10. This plate 114 is substantially similar to that described above, being rotatable about three mutually perpendicular axes A, B and C that intersect through fulcrum 120, and further includes a pair of longitudinal slots 101 and 103 in which a pair of guide members 105 and 107 are slidably mounted for movement between the front edge 118 and the rear edge 119. In order to further facilitate the positioning of the dental arch models, especially large dental casts and those having severe occlusal abnormalities, each elongated member 105 and 107 also includes an axial rod 109 and 111, respectively, that is substantially normal to the top surface 113 and 115 of each respective member 105 and 107. Axial rods 109 and 111 may conveniently be in the form of pins or threaded members. Each elongated member 105 and 107 may be rotated about its respective axial rod 109 and 111 and set to a desired position, such as by a set screw or the like, to ensure that appropriate points of the dental arch model positioned thereupon contact the top surface 113 and 115 of each member 105 and 107, respectively. In this manner, the apparatus of the present invention may conveniently accomodate nearly any size and configuration of dental arch model, with the top surface 113 and 115 of each respective guide member 105 and 107 and the platform top surface 116 proximal fulcrum 120, which may also be elevated above surface 116 the same amount as surfaces 113 and 115, defining the occlusal contact plane for the arch model. Accordingly, each guide member 105 and 107 may conveniently be moved along its respective slot 101 and 103 and then rotated about its respective axial rod 109 and 111 such that predetermined points of the arch model engage the defined occlusal contact plane.

To further assist with the placement of the arch model on plate 114, indicia 189 may be provided, such as a channel formed through plate 114 and intersecting plate rear edge 119, to define the midline of plate 114 aligned substantially with fulcrum 120. An elongated rod may be attached substantially normal to the plate top surface 116 and conveniently moved along channel 189 toward and away from fulcrum 120 to further facilitate the positioning of the arch model on plate 114.

Referring back to FIGS. 1–5 and 9, an arm, generally indicated as 22, is movably attached to the plate 14 to position the fulcrum point 20 at a predetermined position.

The arm 22 should be dimensioned and configured for removable attachment to the particular articulator 12 in which the dental arch model 13 is to be positioned. In addition, the arm 22 may provide for spacial positioning of the plate 14, such as by linear adjustment of fulcrum 20 along three mutually perpendicular directions that preferably include substantially vertical, horizontal left to right and horizontal front to back. Of course, other combinations of spacial measurements may be used to position fulcrum 20. In the preferred embodiment shown in the figures, three positioning elements 24, 26 and 28, which may conveniently be in the form of slides, threaded members or other adjustment devices, may be used for adjusting the linear positioning of the fulcrum 20 along three mutually perpendicular directions.

The apparatus 10 of the present invention also includes means for rotating the top surface 16 of plate 14, which means may suitably be angular joints, such as hinges threaded fasteners or other rotatable elements, about three generally mutually perpendicular axes, indicated in FIGS. 1-5 and 9-16 as A, B, and C, that intersect through the fulcrum point 20. By providing such adjustable rotation about axes A, B, and C, the present invention may be adjusted to simulate the angular position of the occlusal contact plane of the maxillary dental arch that is represented by arch model 13 in FIG. 1. In addition, the linear adjustment of the plate 14 provided by positioning elements 24, 26 and 28 preferably occurs along at least one, although preferably each, of these axes.

In the preferred embodiment of the present invention illustrated in FIGS. 1-5 and 9, the arm 22 is attached to the plate 14 such that the plate 14 may rotate about the three axes A, B, and C, respectively. In addition to the angular rotation about the three axes, the arm 22 also preferably provides means for vertically adjusting the fulcrum point 20 of the plate 14 along axis A, such as adjustable positioning element, indicated as 24. The arm 22 also includes means for horizontally adjusting the fulcrum point along at least one of the axes B and C, indicated as 26 and 28, respectively. In the preferred embodiment, the fulcrum point 20 of the plate 14 may be moved horizontally along axis B by adjusting positioning element 26 and may be moved horizontally along axis C by adjusting positioning element 28. Positioning elements 24, 26, and 28 may conveniently be in the form of slides, threaded members or other adjustment devices for adjusting the linear position of the plate fulcrum along the axes A, B and C. In addition, these adjustments preferably are made with respect to measurements of the maxillary dental arch represented by the arch model 13 relative to predetermined anatomical features.

As shown in FIG. 1, the arm 22 also acts as an interface to the articulator 12 and generally establishes a zero position of the fulcrum point 20 with respect to the articulator 12. The particular attachment of arm 22 to articulator 12 will vary based upon the design of the particular articulator 12. In the preferred embodiment shown in FIGS. 1, 2 and 9, vertical adjustment means 24 is dimensioned and configured to provide the interface to the articulator 12. Each of the positioning elements 24, 26, and 28 will have appropriate zero positions. For example, the zero position for the conventional dental articulators may be related to the condylar hinge axis and for the polycentric hinge joint types the zero position may be related to the superior aspect of the glenoid fossa. Thus, adjustment means 24, 26, and 28 may be accordingly scaled in order to establish a standard zero position for the articulator type used.

In order to rotate plate 14 about each of the axes, the preferred apparatus of the present invention also includes a first means 30, which may conveniently be an angular joint including a set screw, a dial or a knob, for adjustably rotating the top surface 16 of the plate 14 about the substantially horizontal axis B that is aligned through the fulcrum point 20. As shown in the top view of FIGS. 3 and 9, a longitudinal rod 31 aligned with its axis of rotation along axis B preferably connects between first angular joint 30 and the front edge 118 of plate 14 to transfer the rotation of angular joint 30 to the plate 14. The side elevation of FIG. 2 exemplifies the manner in which the plate 14 may rotate about axis B by adjusting the first angular joint 30, which angular joint has been removed from FIG. 2 for the purpose of illustration. Reference numbers 14' and 14" indicate such movement of the plate 14 between two positions. As shown in this embodiment, it will be understood that such angular joints will typically include a dial or knob having a visible scale 36 to control accurately the incremental rotation of plate 14 about axis B.

Similarly shown in FIGS. 1-3 and 9, a second angular joint 32 is positioned along axis C for adjustably rotating the top surface 16 of the plate 14 about the substantially horizontal axis C that is aligned through the fulcrum point 20 and is substantially normal to axes A and B. The preferred embodiment illustrates the second angular joint 32 slidingly attached to the arm 22 along its top surface through positioning element 28. Therefore, due to this attachment, which may be suitably scaled and marked for incremental adjustments, indicated as 37, the angular adjustments about axis C may be achieved. In accordance to the preferred embodiment illustrated in the figures, by appropriately turning the dial of the second angular joint 32 about axis C, such angular rotation is transferred along a longitudinal shaft 33, which is positioned with its axis of rotation along axis C, to the plate 14. In addition, the shaft 33 preferably is attached to the front end of an outer plate housing 39 to which the rotation of rotating means 32 may be transferred, and thereby rotate the plate 14 about axis C. While an outer plate housing 39 is illustrated in the preferred embodiment shown in the figures, alternative embodiments all within the scope of the present invention will be apparent to those skilled in the art. As will be discussed in greater detail below, the angular rotation of plate 14 about axis C in accordance with the present invention is intended to simulate the angular positioning of the occlusal contact plane of a dental arch about the midpoint between the front incisors as viewed from an anterior-posterior or a posterior-anterior perspective.

FIGS. 1, 2, 4 and 9 illustrate a third angular joint 34 positioned along the substantially vertical axis A that is aligned substantially normal to both axes B and C for rotating the plate 14 about axis A. As discussed with respect to angular joints 30 and 32, this third angular joint 34 generally transfers the angular rotation about axis A, which may be introduced at the dial of third angular joint 34, along a longitudinal shaft 35 to the plate 14. Preferably, the shaft 35 is positioned with its axis of rotation along axis A and connects the rotating means 34 through the outer plate housing 39 to the inner plate housing 43 to accordingly rotate the plate 14 about axis A. As will be discussed in greater detail below, such rotation of the plate about vertical axis A generally simulates the left to right rotation of the maxillary dental arch in a horizontal plane about the midpoint the front incisors.

As illustrated in the preferred embodiment of the present invention of FIGS. 1-5 and 9, the arm 22 may include each angular joint 30, 32, and 34, providing for the above mentioned rotation about axes B, C, and A, respectively.

While the adjustable rotating means described above as rotating means 30, 32 and 34 may accurately position the plate 14 to represent an individual's occlusal contact plane, alternative means, all within the scope of this invention, will be apparent to those skilled in the art. Suitable alternative means for adjustably rotating the top surface 16 of the plate 14 may include, without limitation, a linear association with respect to a fixed reference of the particular articulator 12 being employed, such as, for example, a plurality of spaced apart, adjustable supports extending from the plate 14 to the articulator 12, whereby the supports may be adjusted such that the plane defined by the top surface 16 may correspond to the position of an individual's occlusal contact plane.

Figure 13:
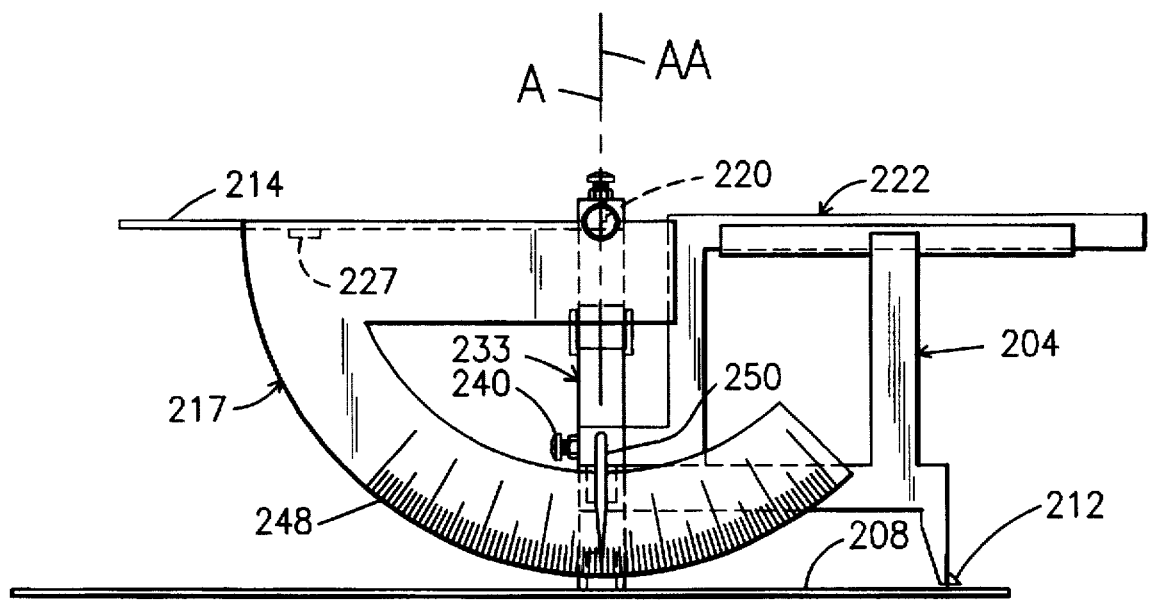
FIG. 13 is a side elevation of the apparatus and calibration stand of FIG. 12.
Figure 12:
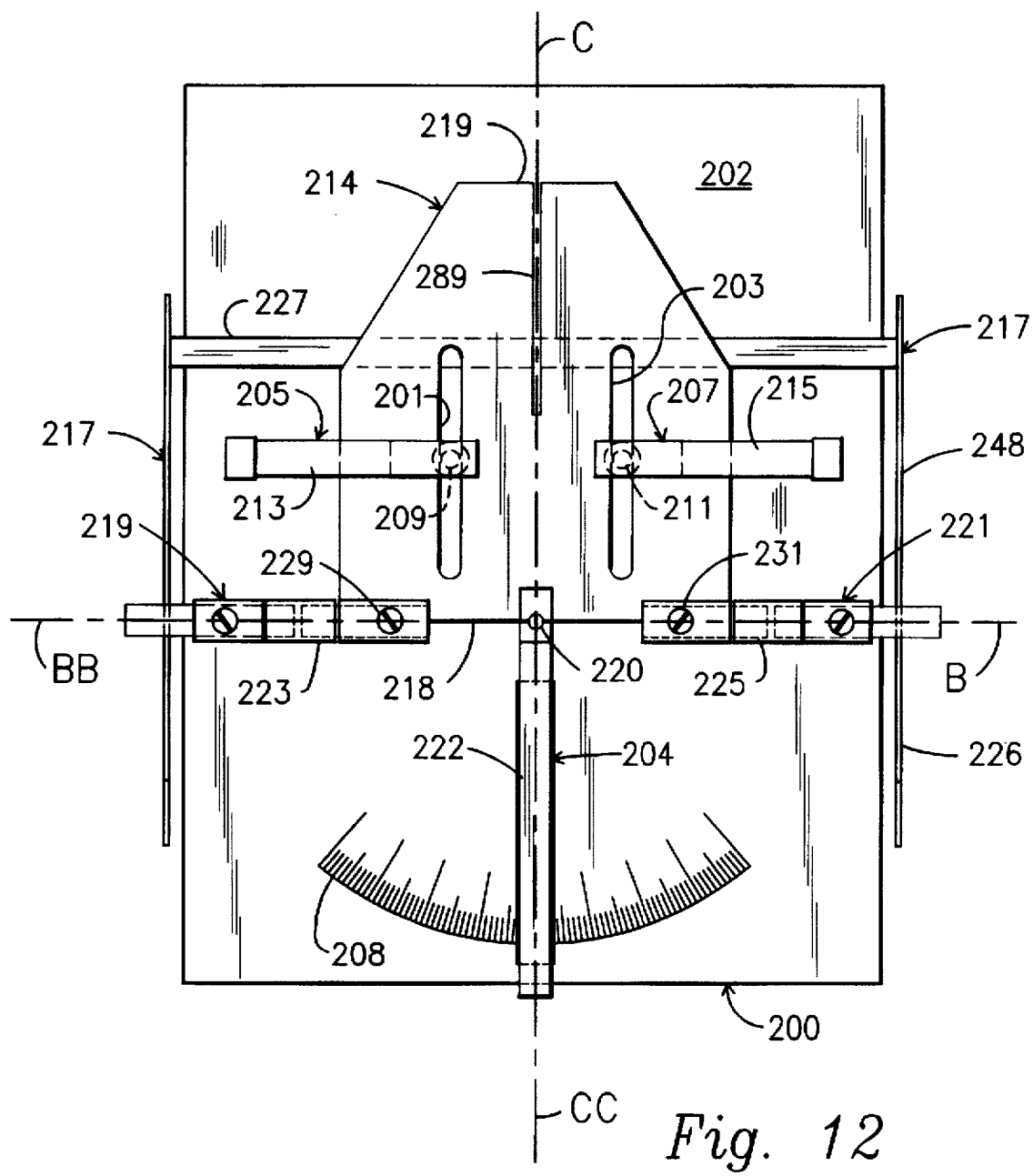
FIG. 12 is a top view of the apparatus of FIG. 10 mounted in a preferred embodiment of a calibration stand.
Figure 15:
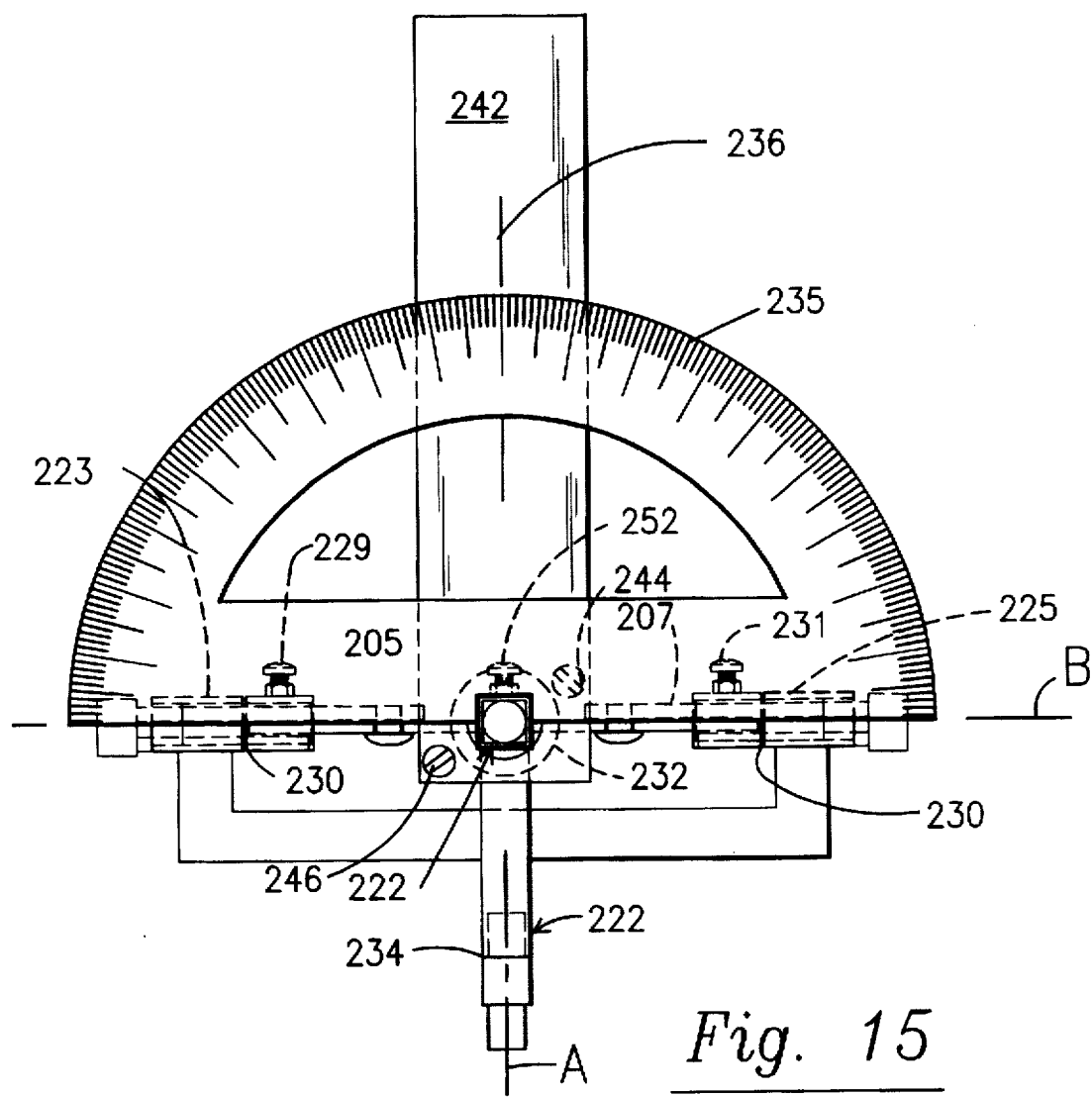
FIG. 15 is a front view of the apparatus of FIG. 10 with a scale and positioning element attached thereto.

FIGS. 12, 13 and 14 illustrate a stand 200 that provides a convenient approach for adjusting plate 214 to simulate the occlusal contact plane of the dental arch prior to attaching the maxillary transfer apparatus 210 to an articulator. In general, calibration stand 200 is dimensioned and configured for receiving the maxillary transfer apparatus 210 of the present invention, and provides a convenient means for adjustably rotating plate 214 about axes A and B.

Calibration stand 200 includes a base 202 and a first support arm 204 that is pivotally attached to base 202 for rotation about axis AA. As illustrated in FIGS. 12, 13 and 14, support arm 204 is dimensioned and configured for receiving and supporting arm 222 of the apparatus of the present invention 210. Accordingly, apparatus 210 may conveniently engage support arm 204 such that apparatus 210 is maintained in a predetermined fixed position with respect to support arm 204, with axis A of apparatus 210 aligned substantially coaxial with axis AA. In addition, stand 200 also includes a pair of supports 237 and 239 extending from base 202 on generally opposed sides of axis AA. Such supports 237 and 239 are dimensioned and configured to engage the lower portion of the plate carriage and hold it at a fixed position generally parallel to axis BB. While the figures illustrate apparatus 210 being maintained in its attachment to support arm 204 by a plurality of sidewall portions extending from support arm 204, it will be understood and appreciated by those skilled in the art that other attachment means, such as pins that engage corresponding holes in apparatus 210 among others, may also be used with equal facility. With apparatus 210 so positioned on support arm 204, support arm 204 may be rotated about axis AA a predetermined amount, which amount may be read from scale 208 by pointer 212, to adjust angular joint 234 and the angular position of plate 214 about axis A. Scale 208 should be calibrated such that the rotation of support arm 204 about axis AA corresponds to the angular rotation of plate 214 about axis A when positioned thereupon. Once the appropriate angle is obtained, locking mechanism 240, which may conveniently be a set screw or other conventional locking means, may be adjusted to substantially fix the rotation of plate number 214 about axis A.

Calibration stand 200 also includes means for adjusting the amount of angular rotation of plate 214 about axis B at first angular joint 232, with such support means being generally illustrated as second support member 217. As illustrated in FIGS. 12, 13 and 14, support member 217 includes a pair of struts 221 and 233 that are attached to and extend substantially normal to base 202 on generally opposed sides of support arm 204. Second member 217 also includes an adjustment platform 227 that is rotatably attached between each strut 221 and 233 and spaced apart from base 202 for rotation about axis BB. Axis BB extends through the top portion of struts 221 and 233 generally parallel to base 202. Second support member 217 further includes an angular scale 248 that is used in connection with alignment pin 250 for determining the amount of angular rotation of platform 227 about axis BB. Alignment pin 250 may conveniently extend normal to base 202 proximal strut 233, and is shown in FIGS. 13 and 14 as being attached to and extending downwardly from strut 233 adjacent scale 248. With the maxillary transfer apparatus 210 positioned on first support arm 204 and on supports 237 and 239 and with axis B aligned substantially with axis BB, the angular rotation of plate 214 about its axis B may be adjusted to a predetermined angle by rotating platform 227 while the plate bottom surface engages platform 227. Once the desired angle is attained, which may be based upon the reading at scale 248 and pin 250, the first angular joint 230 of apparatus 210 may be locked at that angle, such as by a conventional locking mechanism, shown as set screws 229 and 231. Of course, a single locking mechanism may also suffice. In order to align axis B of apparatus 210 with axis BB of calibration stand 200, generally horizontal members extending from the top portion of struts 221 and 233 may conveniently engage cylindrical members 223 and 225 of apparatus 210. Cylindrical members 223 and 225, which may conveniently be rectangular or cylindrical members that are substantially coaxial with axis B, may rotatably engage the top portion of struts 221 and 233 such that axis B is substantially coaxial with axis BB. Thus, it is apparent that plate 214 may rotate about axis BB and axis B by loosening locking mechanism 229 and 231 and then re-tightening once at the desired angle.

When using calibration stand 200, the second angular joint 232 for rotating plate 214 about axis C is illustrated as being part of arm 22, and, which may be attached to or integral therewith. In the preferred embodiment illustrated in FIGS. 11, 12, 13 and 15, second angular joint 232 is formed as part of vertical plate 242 that includes an aperture dimensioned and configured for receiving the horizontal portion of arm 222, such that axis C is coaxial to the center of angular joint 232 and such that vertical plate 242 may conveniently be linearly adjusted along arm 222, thereby defining positioning element 228. Preferably, apparatus 210 is dimensioned and configured such that the longitudinal axis of the horizontal portion of arm 222 is substantially coaxial with both axis C and angular joint 232. This may be accomplished by configuring arm 222 such that its horizontal longitudinal axis intersects fulcrum 220. The angle of rotation of angular joint 232 about axis C may be set by comparing scale 235 with indicia 236, which may conveniently be a visible line positioned vertically along element 242. Once the desired angle is adjusted, angular joint 232 may be fixed by a conventional locking mechanism, such as by tightening set screws 244 and 246. Scale 235 may be removed from arm 222 prior to attaching the arm to a dental articulator. Accordingly, by utilizing the calibration stand 200 along with scale 235, the angular positioning of plate 214 about axis A, B and C may conveniently be set to define and simulate the angular positioning of a patient's occlusal contact plane prior to transferring the maxillary transfer apparatus 210 to the dental articulator.

Figure 16:
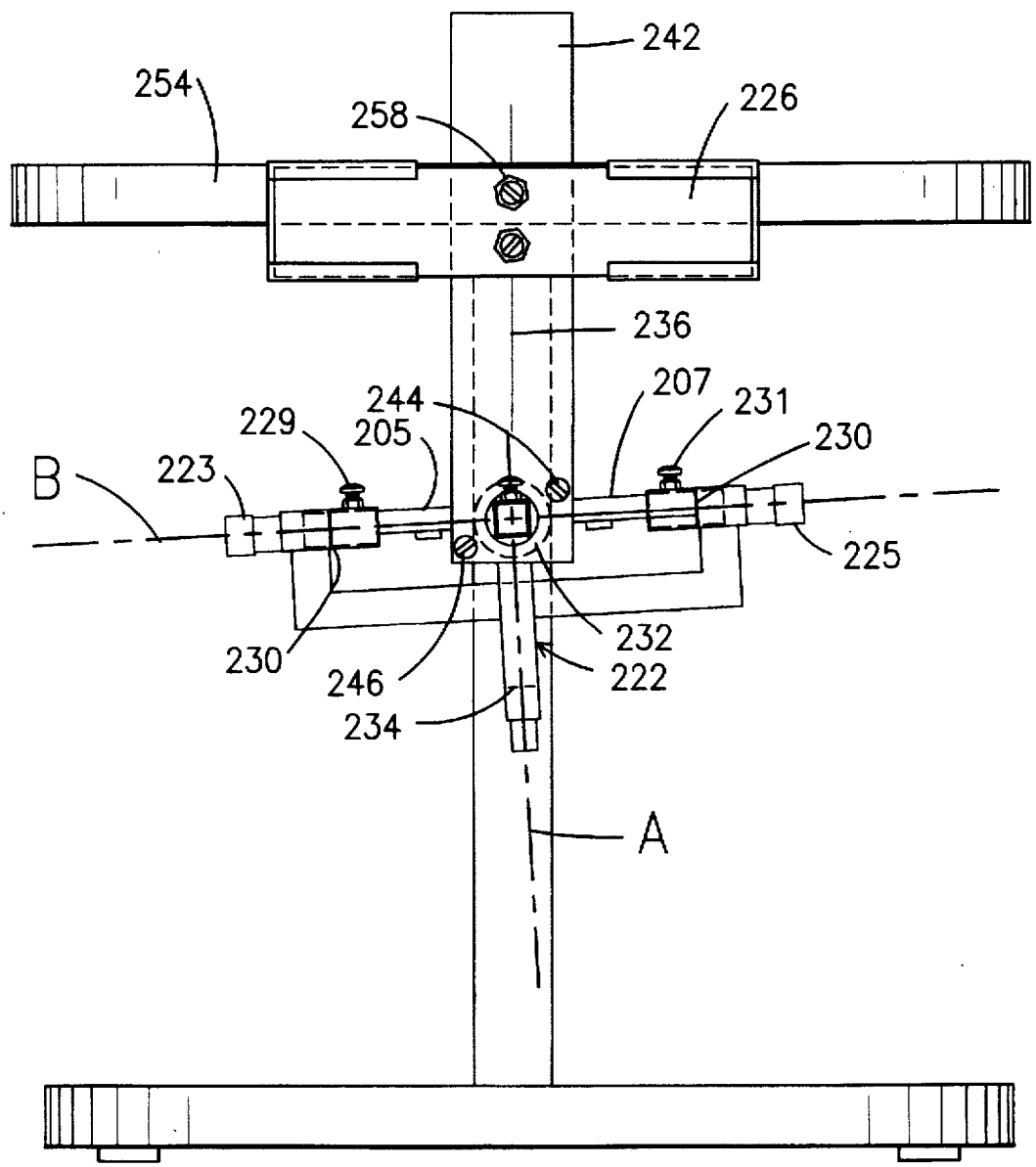
FIG. 16 is a front view of a preferred embodiment of the apparatus of FIG. 10 attached to a dental articulator.

FIG. 16 illustrates apparatus 210 positioned in an appropriate dental articulator 254, such as by attaching vertical attachment member 242 to the front vertical guide pin of articulator 254. The attachment between element 242 and dental articulator 254 defines positioning element 224 for linearly positioning the fulcrum 220 along axis A. In order to provide precise linear adjustment along axis A, vertical plate 242 preferably includes a calibrated linear scale dimensioned with respect to the articulator. As is also shown in FIG. 16, the apparatus 210 also preferably includes positioning element 226, which is shown as a generally rectangular elongated bar that is substantially normal in its orientation with respect to member 242. Positioning element 226 provides for linear adjustment of fulcrum 220 along axis B. The linear movement of plate 214 along axis B is accomplished by the slidable attachment of positioning element 226 to member 242 that permits movement therebetween substantially parallel to axis B. In addition, the vertical adjustment of fulcrum 220 may also be accomplished by providing for movement between positioning element 226 and member 242 substantially parallel to axis A or between articulator 254 and member 242. Once the desired linear measurements along axes A and B are at the desired positions, the appropriate locking mechanism, suitably set screw 258 and 259 may be used to fix apparatus 210 at that position.

In order to position dental arch model 13 in accordance with the present invention, appropriate anatomic landmarks need to be identified as well as their linear and angular relationships quantified. Once appropriate measurements have been obtained, the dental arch model 13 may then be positioned upon the top surface 16 of the plate 14 with the midpoint 42 between the front incisors aligned with the fulcrum point 20, as shown in FIG. 1.

It will be understood and appreciated by those skilled in the art that the identification and quantification of the linear and angular anatomical relationships may be accomplished clinically directly from the patient, radiographically, by sonic digitization or by other advancing technologies, such as teleradiology. It also will be understood further that the anatomical landmarks identified and described with respect to the present invention are merely illustrative of the concept of the present invention and that other references may be used with equal facility all within the scope of the present invention. The preferred embodiment of the present invention utilizes the relationships between three linear measurements related to the midpoint between the front incisors and three angular measurements of the occlusal contact plane of a patient's maxillary dental arch. These quantified measurements may be transferred to the apparatus of the present invention, which may be appropriately attached to a dental articulator 12, as shown in FIG. 1. In accordance with the preferred embodiment of the present invention, these measurements may conveniently be obtained from three cephalograms represented by FIGS. 6, 7 and 8.

Figure 6:
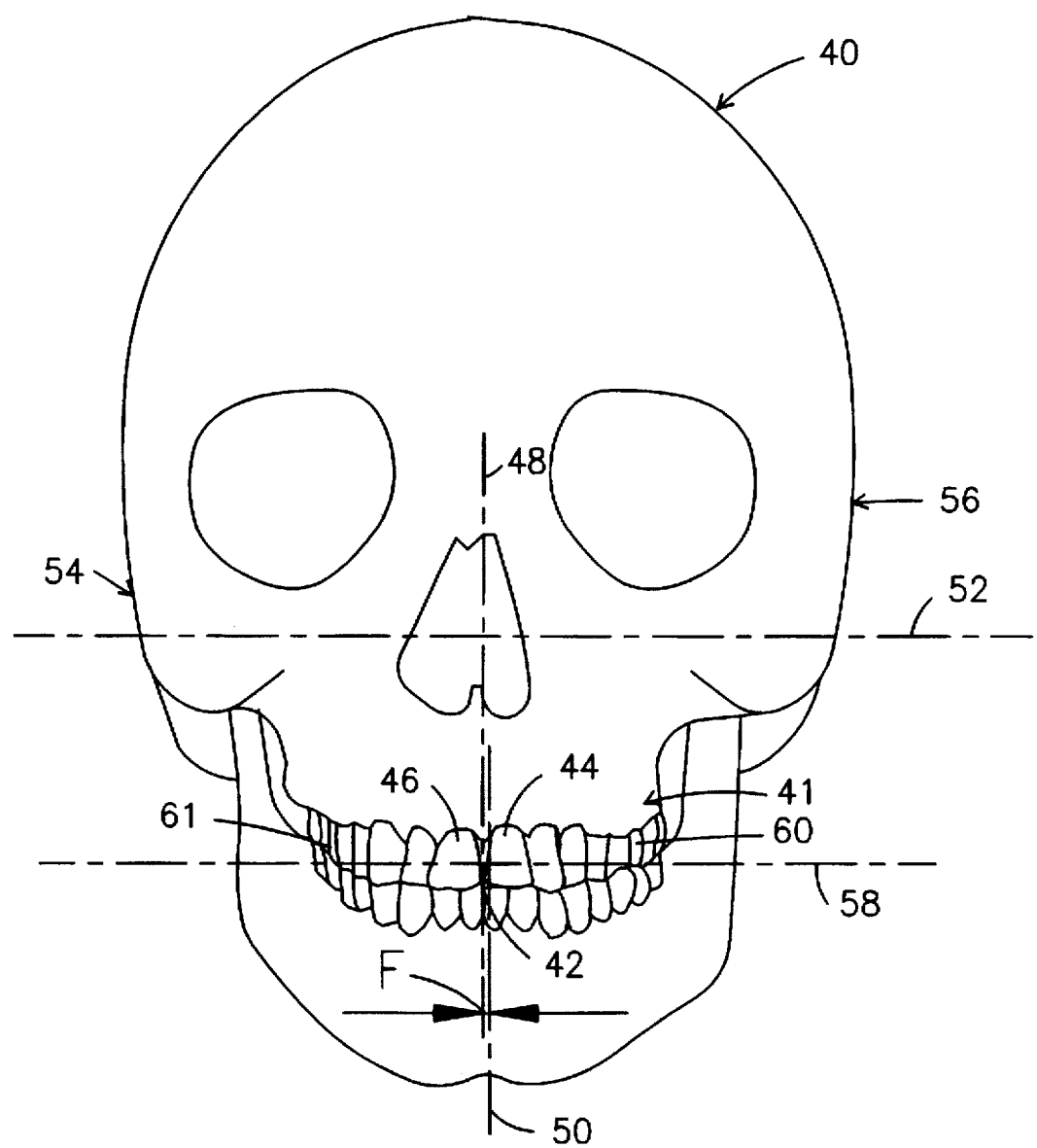
FIG. 6 is a posterior-anterior two-dimensional representation of a cephalogram illustrating preferred reference lines in accordance with the present invention.

From the posterior-anterior view of FIG. 6, one linear measurement and one angular measurement are preferably obtained. The first linear measurement that is to be transferred to the left-to-right positioning element 26 is the distance between the midpoint 42 between the front incisors and the substantially vertical mid-line reference line 48, which may suitably be positioned upon the odontoid process. This distance, indicated as F, may be measured from a cephalogram as the distance between the vertical mid-line 48 and the substantially parallel line 50 drawn through the midpoint 42 between the left and right front incisor 44 and 46, respectively. In accordance with the preferred embodiment of the present invention, this distance F is transferred to the positioning element 26 or 226 of the transfer apparatus 10 or 210, which may be adjusted generally along axis B. In this manner, the apparatus of the present invention simulates the relative distance between the midpoint 42 between the front incisors 44 and 46 of a patient's maxillary dental arch 41 and the predetermined mid-line 48 of the skull 40.

The angle obtained from FIG. 6 is the angular relationship between a first predetermined substantially horizontal reference line 52 extending between the right and left lateral regions 54 and 56, respectively, of the skull 40 and line 58 defining the left-right (anterior-posterior) projection of the occlusal contact plane. As illustrated in FIG. 6, the reference line corresponding to the occlusal contact plane line 58 is preferably defined by connecting the first molar cusp tips 60 and 61 on the respective opposing left and right sides of the maxilla 41. It will be understood, however, that any two points along the occlusal contact plane that are appropriately spaced apart from the midpoint 42 may also adequately represent the occlusal contact plane. The angular measurement is related to the angular relationship between the substantially horizontal reference line 52 and the occlusal contact plane line 58. The horizontal line 52 may be established, for example, by appropriately placing led markers on a patient prior to taking a radiograph, by locating the superior aspect of the glenoid fossa on the radiograph or locating the so-called condylar hinge axis. The particular horizontal reference line selected will typically vary based upon the type of dental articulator 12 being used to position the dental casts. The angle defined by the angular relationship of lines 52 and 58 is appropriately transferred to the second angular joint 32, 132 and 232 that rotates about axis C of the apparatus shown in FIGS. 1-3, 9, 10 and 14-16. In turn, by accordingly adjusting angular joint, the plate 14, 114 or 214 rotates about axis C further simulating the angular positioning of the occlusal contact plane.

Because the occlusal contact plane defined by the maxilla 41 will vary from patient to patient, each angular joint will typically be scaled such that some zero reference angle will typically correspond to either a zero degree measurement or some average amount of angular rotation along each particular axis.

Figure 7:
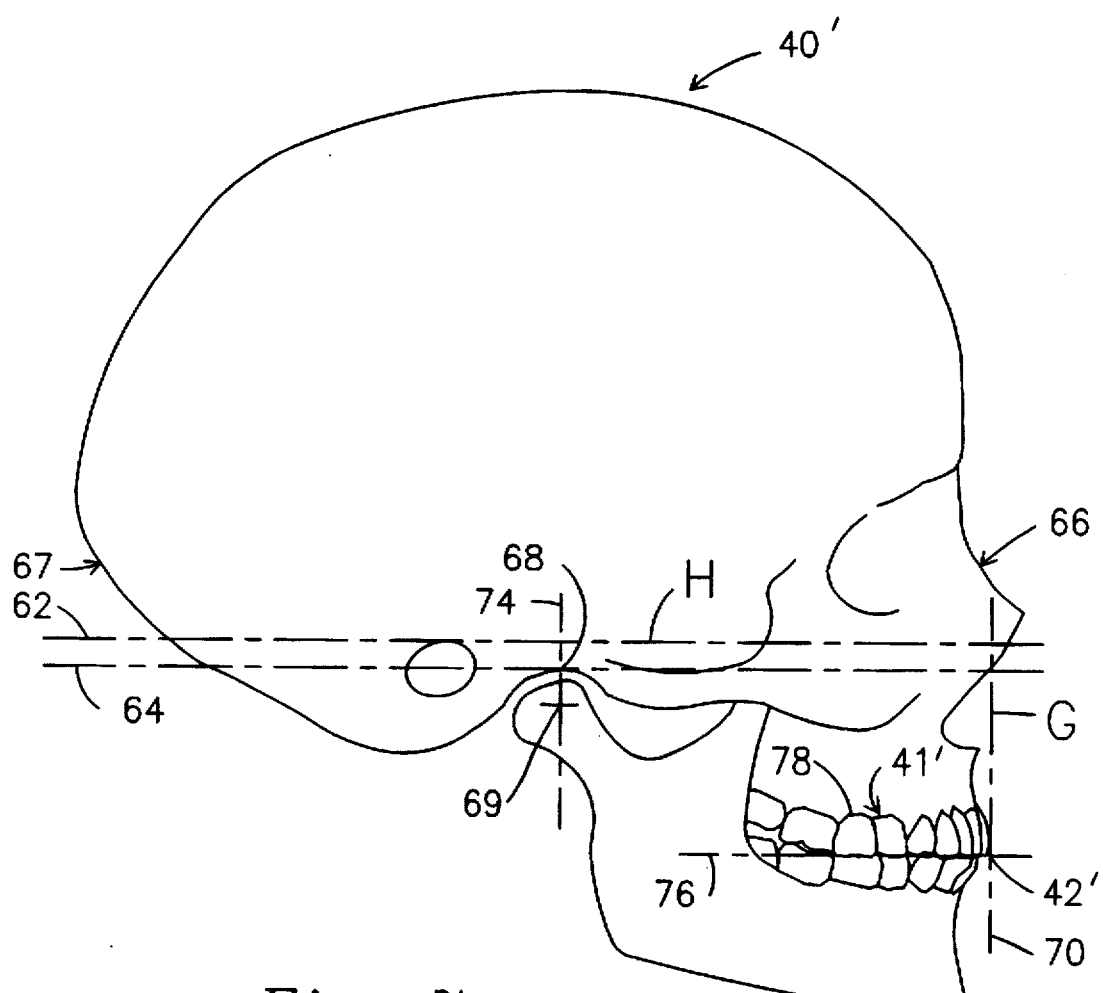
FIG. 7 is a lateral two-dimensional representation of a cephalogram illustrating preferred reference lines in accordance with the present invention.

In accordance with the preferred embodiment of the invention, one angular measurement and the remaining two linear measurements may be obtained from a sagittal or lateral representation of cephalogram, shown in FIG. 7. A second predetermined substantially horizontal reference line 64 extends between the anterior 66 and the posterior 67 regions of the skull 40'. This horizontal reference line 64 may suitably be drawn parallel to the well known Frankfurt Horizontal 62 and drawn through a predetermined anatomical reference point such as, for example, the superior aspect of the glenoid fossa 68, as in FIG. 7, or the mid-condyle "hinge axis" 69. The two linear measurements, G and H, are obtained by relating the midpoint between the front incisors to one of the predetermined points 68 or 69. Perhaps the simplest approach is to measure from the midpoint between the front incisors to reference line 64 along a substantially vertical reference line 70 that is aligned substantially perpendicular to reference line 64. This measurement G, corresponding to the vertical component of the actual distance between midpoint 42' and the reference point 68 or 69, may then be transferred to positioning element 24 or 224 of the apparatus 10, 110 or 210 of the present invention by vertically positioning the plate 14 or 214 according to the distance G (see FIGS. 1, 2, 7, 9 and 16).

The next linear measurement H that may be obtained from the sagittal view of FIG. 7, is the respective horizontal distance between the midpoint 42' between the front incisors taken along the front incisal edge of the maxilla 41' and a respective predetermined reference point, which may suitably be the superior aspect of the glenoid fossa 68 or the mid-condyle hinge axis 69. Those skilled in the art will appreciate, however, that any identifiable reference point, anatomical or otherwise, may be used with equal facility provided such reference point generally be reproducible in the dental articulator 12 used to position the dental arch models. This distance between the midpoint between the front incisor and the predetermined reference point 68 or 69 is indicated by dimension line H and corresponds to a horizontal component of the distance between the midpoint 42' and the reference point, 68 or 69. The relatively short vertical reference line 74 is added to FIG. 7 to illustrate the location of the predetermined reference point 68 or 69 better.

Once the distance H has been obtained, it is accordingly transferred to the maxillary transfer apparatus 10, 110 or 210 shown in the views of FIGS. 1, 2, 3, 9, 10, 15 and 16. Specifically, the value H is utilized by the positioning element 28, 128 or 228 by positioning the fulcrum 20, 120 or 220 along axis C according to measurement H.

A sagittal occlusal plane angle is obtained from the view of FIG. 7 to simulate the angular relationship between occlusal contact plane and a horizontal reference line such as line 64. The sagittal representation of the occlusal contact plane is defined by a line connecting the incisal edge of the midpoint 42' between the front incisors to a predetermined point positioned along the occlusal contact plane 76 distal the midpoint 42'. A preferred such reference point is the tip of the first molar cusp 78, but it will be understood and appreciated by those skilled in the art that other suitable methods, such as facebow recording, exist for finding the sagittal occlusal plane angle. The angle is defined by the angular relationship between the plane 76 and a substantially horizontal reference line such as reference line 64. This angle is preferably the average of two separate angles formed with the left and the right first molar lingual cusp tips individually to the midpoint 42' and reference line 64. The left and the right molars are actually lateral to the axis of the occlusal contact plane that extends through the midpoint 42', which may correspond the fulcrum point 20, 120 or 220 of the apparatus 10, 110 or 210. Once the sagittal occlusal plane angle is determined, it may be transferred to the maxillary transfer apparatus 10 or 210 of the present invention by accordingly rotating the first angular joint 30, 130 or 230, thereby rotating the plate about axis B.

Figure 8:
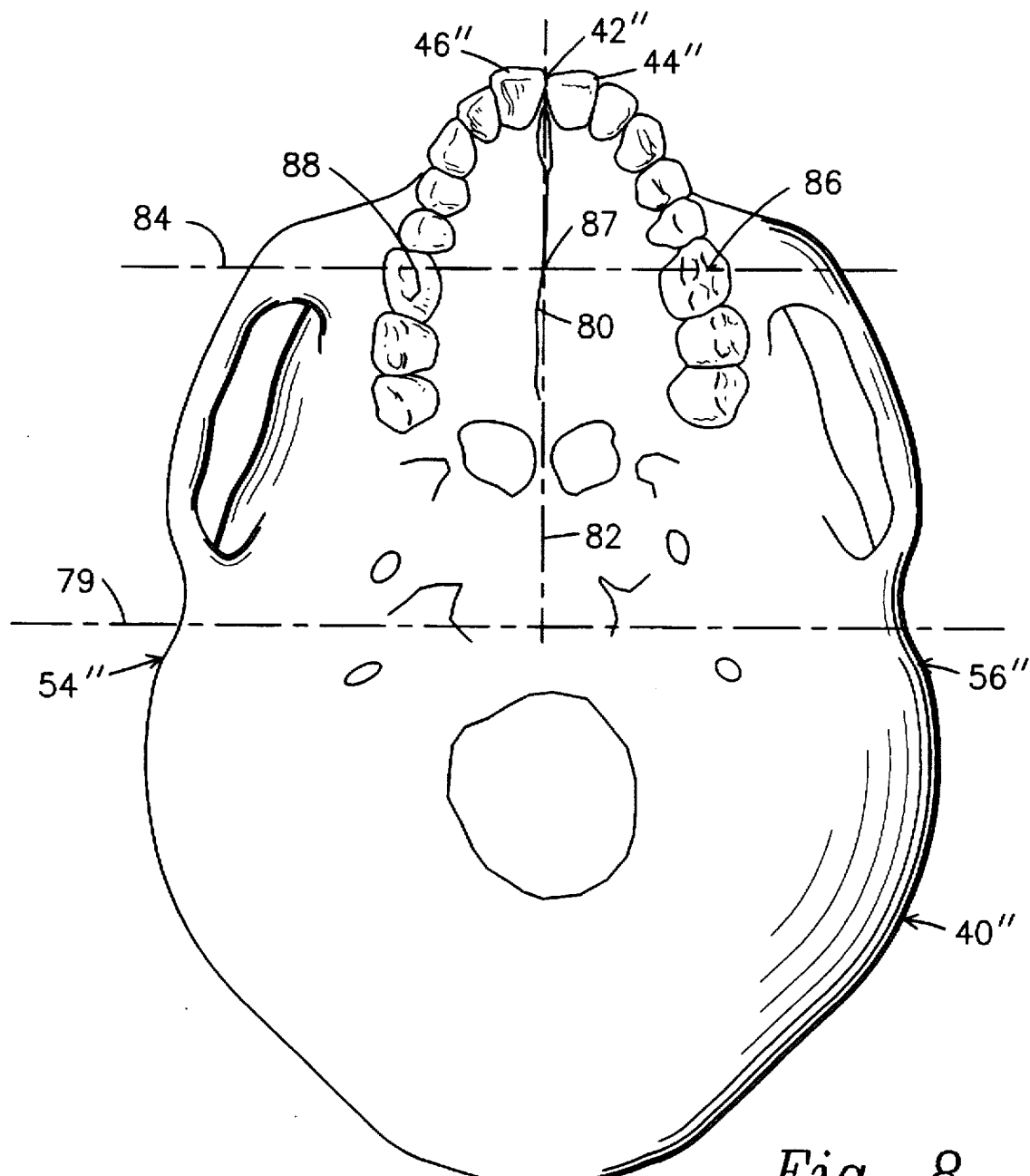
FIG. 8 is a submento-vertex two dimensional representation of a cephalogram illustrating preferred reference lines in accordance with the present invention.

FIG. 8 illustrates a submento vertex two dimensional representation of a cephalogram from which the final angular measurement may be obtained. This angle generally relates to the left to right rotation of the maxilla in a horizontal plane about the midpoint 42" between the left and right front incisors 44" and 46", respectively. As illustrated in FIG. 8, the midpalatal suture line 80 identifies a readily available midline reference of the skull 40, that may also be located conveniently on a properly made maxillary dental arch model. A reference line 82 is defined by extending a line through the midpoint 42" and a central reference point 87 that is positioned generally intermediate the midpoint 42" and the horizontal reference line 79. As shown in the preferred embodiment illustrated in FIG. 8, a line 84 is defined by connecting the left and right lingual cusp tips 86 and 88, respectively, and intersects the midpalatal suture line 80 to define the central reference point 87. The angle defined by intersection between reference line 82 and reference line 79 indicates the amount of angular rotation that is to be transferred to the third angular joint 34, 134 or 234 of the apparatus 10, 110 or 210, shown in FIGS. 1-4, 9, 11 and 14-16. Thus, once this angle is determined, either clinically or radiographically, the third angular joint 34, 134 or 234 may accordingly be adjusted, thereby rotating the plate 14, 114 or 214 about axis A. This generally simulates the rotation of the dental arch along the occlusal contact plane about a generally vertical line through the midpoint between front incisors.

In view of the foregoing detailed description, it will be understood and appreciated that a plate may be adjusted according to three linear and three angular measurements to simulate the positioning of a dental arch in a patient's skull. The corresponding dental cast may be positioned on the plate, either before or after the appropriate adjustments have been made to the plate, with the mid-point between the front incisors of the dental cast aligned with the fulcrum point of the plate. In order to more accurately simulate the position of the occlusal contact plane, the mid-palatal suture line, shown in FIG. 8, may also be used to align the dental cast on the top surface of the plate. This may be accomplished, for example, by positioning indicia 89, 189 or 289, which may be an alignment mark or the like, on the top surface of the plate aligned with axis C intermediate the front edge and the rear edge of the plate. Indicia 89 may also be a channel formed through plate 14 in which an adjustment rod may be positioned. A technician may locate the suture line on the arch model and then appropriately align the arch model with the indicia upon the top surface of the plate.

Once the dental arch model has been properly positioned on the plate and the plate has been adjusted according to the three linear and three angular measurements, the cast may be affixed to the mounting plate 90, shown in FIG. 1. This may conveniently be accomplished by filling the space between the mounting plate 90 and the dental arch 13 with a suitable dental plaster.

It will be understood and appreciated that the apparatus of the present invention may also be used in conjunction with conventional facebow recording and transferring. In one such application, for example, after the maxillary dental arch model has been transferred to the dental articulator via the facebow, the apparatus of the present invention may be used to record the aforementioned three linear and three angular measurements such that positioning of the maxillary dental arch model may be reproduced in the articulator without the continued need for the facebow.

In addition, where a patient is missing a tooth or teeth, the appropriate area may be identified and filled with a wax representation of the missing tooth identifying the particular reference point with an appropriate led marker. In other situations, selecting alternative reference points may prove easier.

While the foregoing describes a particularly preferred embodiment of the apparatus and the method of the present invention, it will be understood that numerous variations and modifications of the present invention, all within the scope of this invention, will be readily apparent to those skilled in the art. All such modifications and variations are considered to be fully within the scope of this invention. Accordingly, the forgoing detailed description is to be considered illustrative only of the principles of this invention and not be limitive thereof. It is also to be understood that the following claims are intended to cover all the generic and specific features of the invention herein described, and all statements of the scope of the invention, which, as a matter of language might be said to fall therebetween. The scope of the present invention is to be determined solely by the claims appended hereto.

What is claimed is:

1. A maxillary transfer apparatus primarily intended for positioning a maxillary dental arch model in a dental articulator to simulate the positioning of a maxillary dental arch in a skull, said apparatus comprising:

an adjustable platform for receiving the maxillary dental arch model, said platform having a generally planar top surface and a front edge, with a fulcrum positioned proximal to said front edge of said platform;

an arm attached to said platform to position said fulcrum at a predetermined position, said arm being dimensioned and configured for removable attachment to the articulator; and means for adjustably rotating said top surface of said platform about three generally mutually perpendicular axes that intersect at said fulcrum, said arm including means to linearly adjust said fulcrum along at least one of said axes, whereby the platform may be adjusted to simulate the positioning of the occlusal contact plane of a maxillary dental arch.

2. An apparatus as in claim 1 wherein said rotating means further comprises a first joint for adjustably rotating said platform to a predetermined angle about a first axis, said first axis being aligned through said fulcrum.

3. An apparatus as in claim 2 wherein said rotating means further comprises a second joint for adjustably rotating said platform about a second axis, said second axis being aligned through said fulcrum and substantially normal to said first axis.

4. An apparatus as in claim 3 wherein said rotating means further comprises a third joint for adjustably rotating said platform about a third axis, said third axis being aligned substantially normal to said first axis, substantially normal to said second axis, and through said fulcrum.

5. An apparatus as in claim 4 wherein said arm is attached to said platform such that said platform may rotate about each of said axes intersecting through said fulcrum.

6. An apparatus as in claim 5 wherein said arm further comprises at least one of said first joint, said second joint and said third joint.

7. An apparatus as in claim 6 wherein said arm further comprises a first positioning element for adjusting the position of said fulcrum along said first axis.

8. An apparatus as in claim 6 wherein said arm further comprises a second positioning element for adjusting the position of said fulcrum along said second axis.

9. An apparatus as in claim 6 wherein said arm further comprises a third positioning element for adjusting the position of said fulcrum along said third axis.

10. An apparatus as in claim 1 wherein said platform further comprises a rear edge and an indicia positioned intermediate said front edge and said rear edge of said platform for aligning the arch model upon said top surface.

11. An apparatus as in claim 10 further comprising a pair of guide members having a top surface, said pair of guide members being slidably mounted to said platform, with each guide member being moveable between said front edge and said rear edge of said platform.

12. An apparatus as in claim 11 wherein each guide member comprises an elongated member having a substantially planar top surface generally parallel to said platform top surface.

13. An apparatus as in claim 12 wherein each elongated member further comprises an axis substantially normal to said elongated member top surface, with each elongated member being rotatable about its respective axis in a plane substantially parallel to said platform top surface.

14. A maxillary transfer apparatus primarily intended for positioning a maxillary dental arch model in a dental articulator to simulate the positioning of a maxillary dental arch in a skull, said apparatus comprising:

a platform having substantially planar top surface and a fulcrum;

a first joint for adjustably rotating said platform about a first axis, said first axis intersecting through said fulcrum;

a second joint for adjustably rotating said platform about a second axis, said second axis being substantially normal to said first axis and intersecting through said fulcrum;

a third joint for adjustably rotating said platform about a third axis, said third axis being substantially normal to said first axis and to said second axis and intersecting through said fulcrum; and an arm removably attachable to a dental articulator, said arm having a positioning element for linearly positioning said platform along at least one of said first axis, said second axis and said third axis, whereby the first joint, the second joint, the third joint and the guide may be adjusted to simulate the positioning of the occlusal contact plane.

15. A maxillary transfer apparatus as in claim 14 wherein said platform further comprises a front edge and a rear edge; and said apparatus further comprises a pair of guide members movedly attached to said platform adjacent said platform top surface, with each said guide member being moveable intermediate said platform front edge and said platform rear edge.

16. A maxillary transfer apparatus as in claim 15 wherein each said guide member further comprises an axis substantially normal to said platform top surface, with each guide member being adjustably rotatable about its respective axis.

17. A maxillary transfer apparatus as in claim 14 wherein said arm further comprises:

a first positioning element for adjusting the position said platform along said first axis, a second positioning element for adjusting the position said platform along said second axis, and a third positioning element for adjusting the position said platform along said third axis.

18. A method for positioning a maxillary dental arch model having a defined midpoint between front incisors in a dental articulator to which a substantially planar surface having a fulcrum point is movably mounted to simulate the positioning of a maxillary dental arch in a skull, the dental arch model having a defined midpoint between front incisors that corresponds to same on the arch represented thereby said method comprising:

positioning the occlusal contact plane of a maxillary dental arch model on the substantially planar surface with the midpoint between the front incisors of the dental arch model substantially aligned with a fulcrum point;

rotating the substantially planar surface about a substantially horizontal first axis aligned through said fulcrum point to simulate the angular positioning of the occlusal contact plane of the dental arch;

rotating the substantially planar surface about a substantially horizontal second axis that is substantially normal to said first axis and aligned through said fulcrum point to simulate the angular positioning of the occlusal contact plane of the dental arch;

rotating the substantially planar surface about a substantially vertical third axis that is substantially normal to said first axis and said second axis and aligned through said fulcrum point to simulate the angular rotation of the dental arch in substantially horizontal plane about the midpoint between the front incisors of the dental arch;

horizontally adjusting said fulcrum point along said second axis to simulate the positioning of the dental arch in the skull; and horizontally adjusting said fulcrum point along said first axis to simulate the positioning of the dental arch in the skull.

19. A method as in claim 18 wherein said planar surface includes a front edge, a rear edge and an indicia positioned proximal said rear edge and wherein said step of positioning further comprises aligning at least a predetermined point of said arch model with said indicia of said planar surface.

20. A method as in claim 18 further comprising the step of vertically positioning said fulcrum point along said third axis to simulate the positioning the dental arch in the skull.

* * * * *

UNITED STATES PATENT AND TRADEMARK OFFICE
CERTIFICATE OF CORRECTION

PATENT NO. : 5,738,515
DATED : April 14, 1998
INVENTOR(S) : Leever

It is certified that error appears in the above-identified patent and that said Letters Patent is hereby corrected as shown below:

On the title page, item [54] and column 1, line 2: in the title, "MIXILLARY" should read -- MAXILLARY --.

Signed and Sealed this

Fifteenth Day of September, 1998

Attest:

BRUCE LEHMAN

Attesting Officer

Commissioner of Patents and Trademarks